(12) United States Patent
Tippey et al.

(10) Patent No.: US 7,700,820 B2
(45) Date of Patent: Apr. 20, 2010

(54) PROCESS FOR CONTROLLING THE QUALITY OF AN ABSORBENT ARTICLE INCLUDING A WETNESS SENSING SYSTEM

(75) Inventors: Darold Dean Tippey, Neenah, WI (US); Perry Allen Bush, Menasha, WI (US); Timothy Patrick Clare, Kernersville, NC (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 605 days.

(21) Appl. No.: 11/607,289

(22) Filed: Nov. 30, 2006

(65) Prior Publication Data
US 2008/0132858 A1    Jun. 5, 2008

(51) Int. Cl.
*A61F 13/15* (2006.01)
(52) U.S. Cl. .......................... 604/361; 604/362; 378/8; 378/9; 378/46; 378/57; 378/92
(58) Field of Classification Search ................. 604/361, 604/362; 378/8, 9, 46, 57, 92
See application file for complete search history.

(56) References Cited

U.S. PATENT DOCUMENTS

| | | | |
|---|---|---|---|
| 2,679,317 A | 5/1954 | Roop | |
| 3,390,769 A | 7/1968 | Tatham et al. | |
| 3,573,455 A | 4/1971 | Suierveld | |
| 3,917,947 A | 11/1975 | Fenton | |
| 3,958,078 A | 5/1976 | Fowler et al. | |
| 4,020,346 A | 4/1977 | Dennis | |
| 4,100,324 A | 7/1978 | Anderson et al. | |
| 4,430,568 A | 2/1984 | Yoshida et al. | |
| 4,484,066 A | 11/1984 | DeBlieux et al. | |
| 4,653,491 A * | 3/1987 | Okada et al. | 128/886 |
| 4,698,832 A * | 10/1987 | Kuusi | 378/46 |
| 4,768,023 A * | 8/1988 | Xie | 340/573.5 |
| 4,768,209 A | 8/1988 | Yu | |
| 4,791,655 A | 12/1988 | Nagata et al. | |
| 4,803,639 A | 2/1989 | Steele et al. | |
| 4,839,943 A | 6/1989 | Leifeld | |

(Continued)

FOREIGN PATENT DOCUMENTS

EP    0 375 157 A2    6/1990

(Continued)

OTHER PUBLICATIONS

"Goring Kerr EZx Contamination Detection System," Thermo Electron Corporation, 4-page product brochure, available prior to the filing date of the current application.

*Primary Examiner*—Tatyana Zalukaeva
*Assistant Examiner*—Ginger T Chapman
(74) *Attorney, Agent, or Firm*—Randall W. Fieldhack

(57) ABSTRACT

The present disclosure is generally directed to a process for controlling the quality of manufactured absorbent articles, the process including incorporating into an absorbent article at least a portion of a wetness sensing system that is configured to detect the presence of a substance, the wetness sensing system comprising at least one metallic conductive element; and passing the absorbent article in proximity to a foreign material sensor employing x-ray technology, the foreign material sensor adapted to detect the presence of foreign material to confirm whether foreign material has been incorporated into the article.

11 Claims, 5 Drawing Sheets

U.S. PATENT DOCUMENTS

| | | | |
|---|---|---|---|
| 4,879,734 A | 11/1989 | Schreckendgust et al. | |
| 4,879,735 A | 11/1989 | Owens | |
| 5,041,721 A | 8/1991 | Smith et al. | |
| 5,187,723 A | 2/1993 | Mueller-Stuercken | |
| 5,247,561 A | 9/1993 | Kotowski | |
| 5,266,928 A * | 11/1993 | Johnson | 340/604 |
| 5,284,703 A | 2/1994 | Everhart et al. | |
| 5,319,547 A | 6/1994 | Krug et al. | |
| 5,350,624 A | 9/1994 | Georger et al. | |
| 5,359,525 A | 10/1994 | Weyenberg | |
| 5,392,032 A * | 2/1995 | Kline et al. | 340/604 |
| 5,483,569 A | 1/1996 | Annis | |
| 5,490,218 A | 2/1996 | Krug et al. | |
| 5,528,647 A | 6/1996 | Anderson et al. | |
| 5,585,603 A | 12/1996 | Vogeley, Jr. | |
| 5,670,694 A * | 9/1997 | Hagedorn et al. | 558/327 |
| 5,803,702 A | 9/1998 | Mullins et al. | |
| 5,838,240 A * | 11/1998 | Johnson | 340/604 |
| 5,910,973 A | 6/1999 | Grodzins | |
| 6,023,497 A | 2/2000 | Takahashi et al. | |
| 6,081,580 A | 6/2000 | Grodzins et al. | |
| 6,097,297 A * | 8/2000 | Fard | 340/604 |
| 6,215,845 B1 | 4/2001 | Knigge | |
| 6,335,960 B2 * | 1/2002 | Knigge et al. | 378/57 |
| 6,352,497 B1 | 3/2002 | Hensley et al. | |
| 6,354,984 B1 | 3/2002 | Hensley et al. | |
| 6,449,334 B1 | 9/2002 | Mazess et al. | |
| 6,512,812 B2 | 1/2003 | Watanabe | |
| 6,574,303 B2 | 6/2003 | Sawada | |
| 6,724,305 B2 * | 4/2004 | Edwards et al. | 340/568.1 |
| 6,812,426 B1 | 11/2004 | Kotowski et al. | |
| 6,820,022 B2 | 11/2004 | Popp et al. | |
| 6,829,516 B2 | 12/2004 | Popp et al. | |
| 6,839,402 B2 | 1/2005 | Stabe et al. | |
| 6,845,278 B2 | 1/2005 | Popp et al. | |
| 6,870,897 B2 * | 3/2005 | Sari-Sarraf et al. | 378/53 |
| 7,060,981 B2 | 6/2006 | Retterath et al. | |
| 2003/0120230 A1 * | 6/2003 | Wulz et al. | 604/368 |
| 2004/0030309 A1 * | 2/2004 | Huang | 604/361 |
| 2004/0051059 A1 * | 3/2004 | Ungpiyakul et al. | 250/559.29 |
| 2004/0113801 A1 * | 6/2004 | Gustafson et al. | 340/604 |
| 2004/0147888 A1 * | 7/2004 | Huang et al. | 604/361 |
| 2004/0220538 A1 * | 11/2004 | Panopoulos | 604/361 |
| 2005/0196580 A1 | 9/2005 | Provost et al. | |
| 2005/0214530 A1 | 9/2005 | Tanaka et al. | |
| 2006/0058745 A1 | 3/2006 | Pires | |
| 2008/0058743 A1 * | 3/2008 | Cohen et al. | 604/361 |
| 2008/0118026 A1 * | 5/2008 | Ainsworth et al. | 378/20 |
| 2009/0036850 A1 * | 2/2009 | Nhan et al. | 604/361 |

FOREIGN PATENT DOCUMENTS

| | | |
|---|---|---|
| EP | 0 285 602 B1 | 7/1992 |
| EP | 1 304 562 A1 | 4/2003 |
| EP | 1 489 530 A1 | 12/2004 |
| EP | 1 550 506 A1 | 7/2005 |
| EP | 1 563 989 A1 | 8/2005 |
| GB | 1 046 443 A | 10/1966 |
| JP | 09-127017 A | 5/1997 |
| JP | 10-132761 A | 5/1998 |
| JP | 2004/028768 A | 1/2004 |
| JP | 2005-008246 A | 1/2005 |
| JP | 2005/024549 A | 1/2005 |
| WO | WO 91/04723 A1 | 4/1991 |
| WO | WO 92/00534 A1 | 1/1992 |
| WO | WO 96/01096 A2 | 1/1996 |
| WO | WO 02/26587 A2 | 4/2002 |
| WO | WO 2005/009844 A1 | 2/2005 |
| WO | WO 2005/083404 A1 | 9/2005 |
| WO | WO 2005/088485 A2 | 9/2005 |

* cited by examiner

PROCESS FOR CONTROLLING THE QUALITY OF AN ABSORBENT ARTICLE INCLUDING A WETNESS SENSING SYSTEM

BACKGROUND

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, super absorbent particles. Many absorbent particles, especially those sold under the trade name HUGGIES™ by the Kimberly-Clark Corporation, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators may include alarm devices that are designed to assist parents or attendants to identify a wet diaper condition early on. The devices produce either a visual or an audible signal.

In some aspects, for instance, conductive threads or foils have been placed in the absorbent articles in the machine direction. The conductive materials serve as conductive leads for a signaling device and form an open circuit in the article that can be closed when a body fluid, such as urine, closes the circuit. In other aspects, disposable absorbent articles such as roll products, wipes products, health care products, incontinence products, feminine care products, diapers and training pants may also include conductive threads or foils.

Incorporating a wetness sensing system into an absorbent article during its manufacture, however, can be problematic with respect to quality control. Standard absorbent articles are typically inspected using a metal detector to detect whether metallic foreign materials of any kind have been introduced into an absorbent article. Metal detectors are also currently used by many manufacturers to confirm that no foreign metal objects have accidentally been placed into any product packages. Absorbent articles or packages including such a foreign materials are culled from the process and disposed of. Absorbent articles incorporating a wetness sensing system including conductive foils or other similar structures, however, may not always be accurately inspected for foreign materials using a metal detector because such absorbent articles already include a certain amount of metal. Thus, a need currently exists for a quality control process that can be used to verify that the absorbent articles incorporating a wetness sensing system do not include foreign materials.

SUMMARY

In general, the present disclosure is directed to a process for controlling the quality of manufactured absorbent articles incorporating a wetness sensing system. As will be described below, a foreign material sensor using x-ray technology may be used to detect the presence of foreign materials in absorbent articles including a wetness sensing system to ensure that the articles have been manufactured with the desired qualities and functions.

The foreign material sensor described herein can be a commercially-available x-ray machine. Such an x-ray inspection is sued to check for foreign materials including metal and mineral clumps such as SAP and glass contaminates.

For example, in one aspect, the present disclosure is directed to a process for controlling the quality of manufactured absorbent articles, the process including incorporating into an absorbent article at least a portion a wetness sensing system that is configured to detect the presence of a substance, the wetness sensing system comprising at least one metallic conductive element; and passing the absorbent article in proximity to a foreign material sensor employing x-ray technology, the foreign material sensor adapted to detect the presence of foreign material to confirm whether foreign material has been incorporated into the article.

In another aspect, the present disclosure is directed to a process for controlling the quality of manufactured absorbent articles, the process including producing absorbent articles incorporating at least a portion of a wetness sensing system, the wetness sensing system being configured to detect the presence of a substance in the absorbent article, the wetness sensing system including at least one metallic conductive element; loading a plurality of the absorbing articles into a package; and passing the package in proximity to a foreign material sensor employing x-ray technology, the foreign material sensor being configured to detect whether the package includes foreign material.

As described above, the process of the present disclosure can be carried out at different times during the manufacture and packaging of the absorbent article. For instance, in one aspect, the absorbent articles can be packaged together and can be passed in proximity to the foreign material sensor prior to being shipped from the location in which the products are packaged.

Of particular advantage, most foreign material sensors can be programmed so as to discriminate between different types of metallic and non-foreign materials and between the amounts of material present in a package. For example, in one aspect, the wetness sensing system incorporated into the absorbent articles may include a ferrous material and the foreign material sensor used to scan the article may be configured to only detect ferrous metals.

Other features and aspects of the present disclosure are discussed in greater detail below.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

Figure 1:
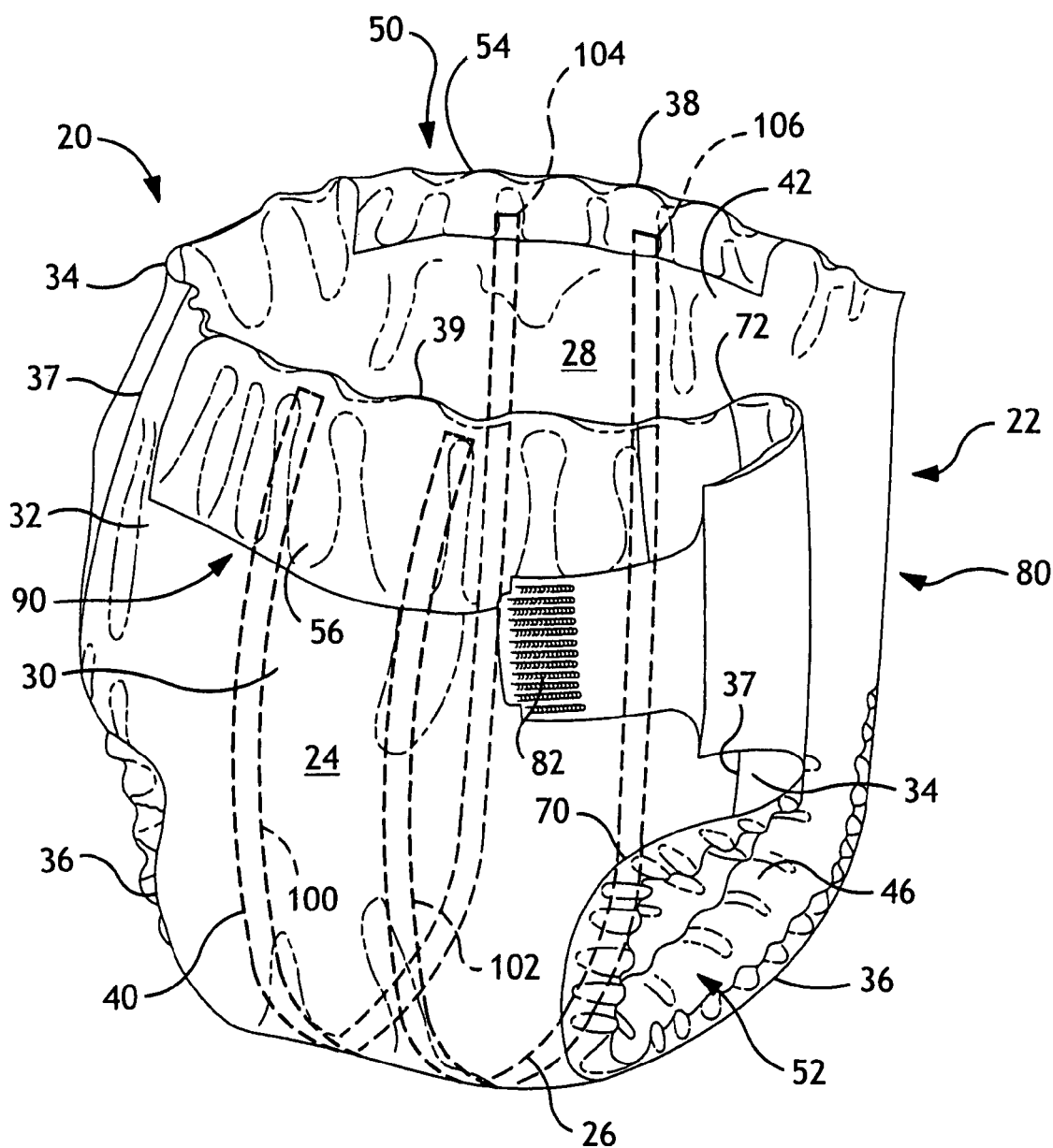
FIG. 1 is a rear perspective view of one aspect of an absorbent article that may be used in the process of the present disclosure.

Repeat use of reference characters in the present specification and drawings is intended to represent the same or analogous features or elements of the present disclosure. The drawings are representational and are not necessarily drawn to scale. Certain proportions thereof may be exaggerated, while others may be minimized.

DETAILED DESCRIPTION

It is to be understood by one of ordinary skill in the art that the present discussion is a description of exemplary aspects only, and is not intended as limiting the broader aspects of the present disclosure.

In general, the present disclosure is directed to a process for producing absorbent articles including a wetness sensing system. More particularly, the present disclosure is directed to a process for ensuring that no foreign material is present within the articles after they have been produced. The quality control process of the present disclosure can be used by manufacturers to ensure that their products meet specifications.

The wetness sensing system incorporated into the absorbent articles may vary dramatically depending upon the particular article being produced and the desired result. Regardless, the wetness sensing system is configured to indicate the presence of a body fluid in the absorbent article or other changes in the condition of the product or wearer. The absorbent article may be, for instance, a diaper, a training pant, an incontinence product, a feminine hygiene product, a medical garment, a bandage, or the like. In one aspect, for instance, the absorbent articles may include an open circuit that becomes closed when a conductive fluid, such as a body fluid, is sensed in between a pair of conductive leads. The conductive leads or other parts of the wetness sensing system can be made from a metallic material. To ensure that the absorbent article with a wetness sensing system has not had any foreign material incorporated into the article, the article can be placed in proximity to a foreign material sensor which senses the presence of any foreign material within the article.

Figure 2:
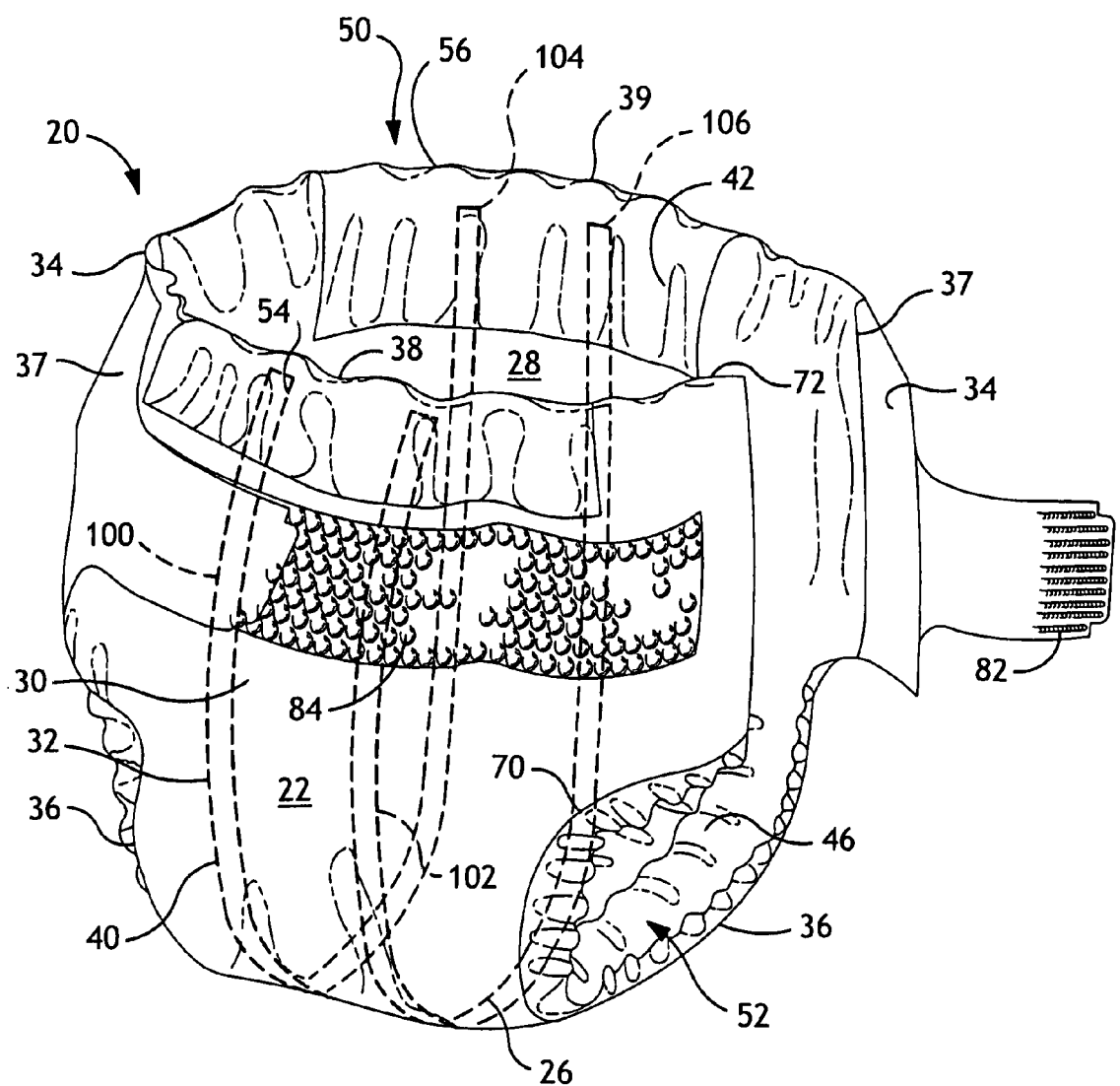
FIG. 2 is a front perspective view of the absorbent article illustrated in FIG. 1.
Figure 3:
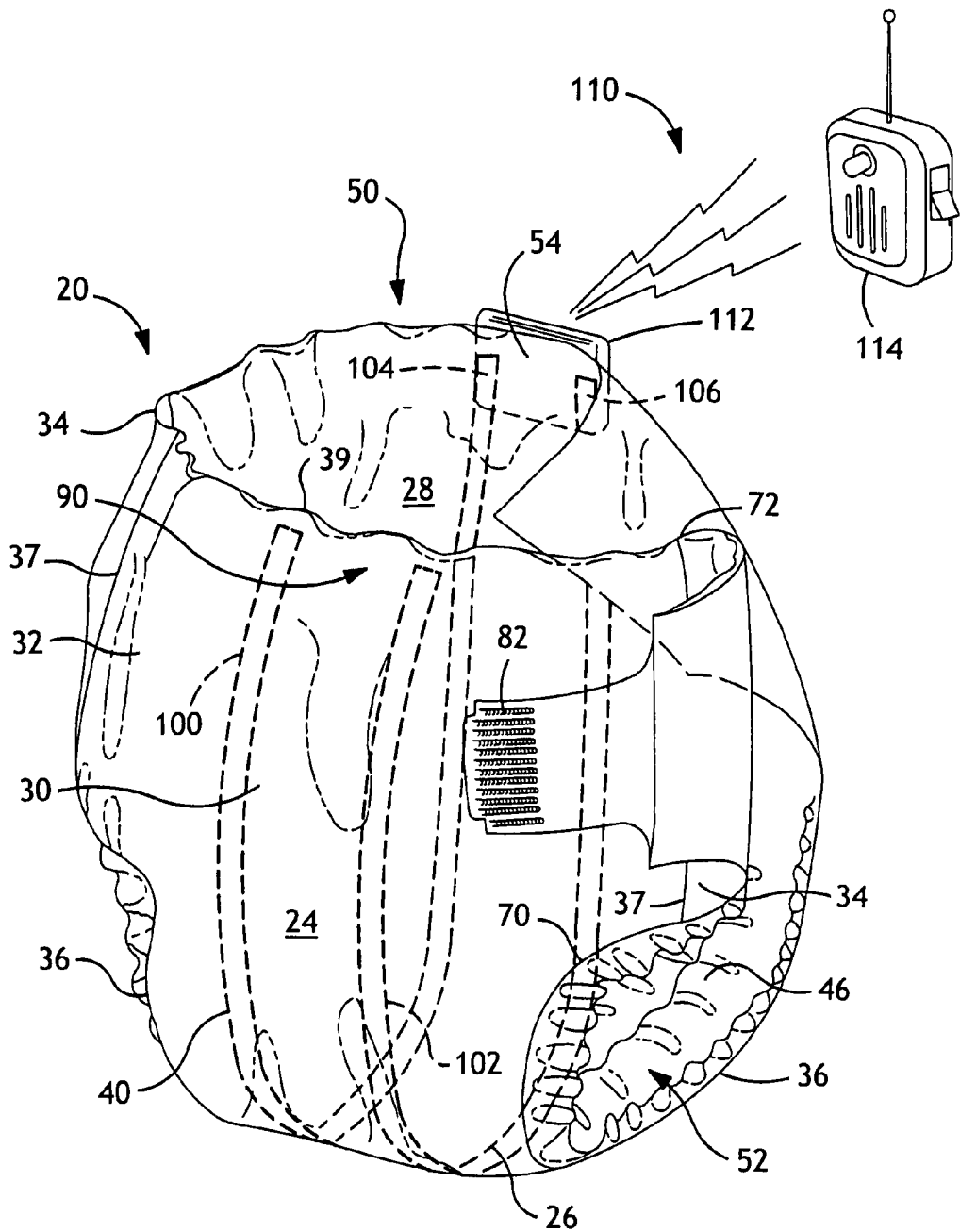
FIG. 3 is a perspective view of the absorbent article illustrated in FIG. 1 further including one aspect of a signaling device.

Referring to FIGS. 1, 2 and 3, for exemplary purposes only, an absorbent article 20 that may be used in the process of the present disclosure shown. For example, in FIGS. 1 and 3, a diaper 20 is illustrated from the rear of the diaper. In FIG. 2, however, the diaper 20 is shown from the front.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this aspect, encompasses the front region 22, the back region 24, and the crotch region 26. The chassis 32 includes an outer cover 40 and a bodyside liner 42 that may be joined to the outer cover 40 in a superimposed relation therewith by adhesives, ultrasonic bonds, thermal bonds or other conventional techniques. The liner 42 may suitably be joined to the outer cover 40 along the perimeter of the chassis 32 to form a front waist seam and a back waist seam. The liner 42 may suitably be joined to the outer cover 40 to form a pair of side seams in the front region 22 and the back region 24. The liner 42 can be generally adapted, i.e., positioned relative to the other components of the article 20, to be disposed toward the wearer's skin during wear of the absorbent article. The chassis 32 may further include an absorbent structure disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis.

To further enhance containment and/or absorption of body exudates, the diaper 20 may also suitably include leg elastic members, as are known to those skilled in the art. The leg elastic members can be operatively joined to the outer cover 40 and/or the bodyside liner 42 and positioned in the crotch region 26 of the absorbent article 20.

As shown, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. The elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative aspect, the elastic side panels may also be integrally formed with the chassis 32. For instance, the side panels 34 may comprise an extension of the bodyside liner 42, of the outer cover 40, or of both the bodyside liner 42 and the outer cover 40.

In the aspects shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the aspects shown in the figures, the side panels are releasably attachable to the front region 22 of the article 20 by the fastening system. It should be understood, however, that in other aspects the side panels may be permanently joined to the chassis 32 at each end. The side panels may be permanently bonded together, for instance, when forming a training pant or absorbent swimwear.

The elastic side panels 34 each have a longitudinal outer edge, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction to provide a better fit around the wearer's legs. However, it is understood that various structures and geometries are suitable without departing from the scope of the present disclosure.

The fastening system 80 may include laterally opposite first fastening components 82 adapted for refastenable engagement to corresponding second fastening components 84. In the aspect shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As described above, the present disclosure is particularly directed to incorporating a wetness indicating system into the absorbent article 20. In this regard, as shown in FIGS. 1-3, the absorbent article 20 includes a first conductive element 100 spaced from a second conductive element 102. In this aspect, the first and second conductive elements 100, 102 extend from the front region 22 of the absorbent article to the back region 24 without intersecting. The conductive elements 100 and 102 can comprise any suitable conductive material, such as a conductive metallic thread or a conductive metallic foil. The first conductive element 100 does not intersect the second conductive element 102 such that they form an open circuit that may be closed, for instance, when a conductive fluid is positioned in between the conductive elements. In other aspects, however, the first conductive element 100 and the second conductive element 102 may be connected to a sensor within the chassis. The sensor may be used to sense changes in temperature or may be used to sense the presence of a particular substance, such as a metabolite.

In the aspect shown in FIG. 1, the conductive elements 100 and 102 extend the entire length of the absorbent article 20. It should be understood, however, that in other aspects the conductive elements may extend only to the crotch region 26 or may extend to any particular place in the absorbent article where a body fluid is intended to be sensed.

The conductive elements 100 and 102 may be incorporated into the chassis 32 at any suitable location as long as the conductive elements are positioned so as to contact a body fluid that is absorbed by the absorbent article 20. In this regard, the conductive elements 100 and 102 generally lie inside the outer cover 40.

For the conductive elements 100 and 102 to be connected to a signaling device, the first conductive element 100 is attached to a first conductive pad member 104, while the second conductive element 102 is connected to a second conductive pad member 106. The pad members 104 and 106 are provided for making a reliable connection between the open circuit formed by the conductive elements to a signaling device that is intended to be installed on the chassis by the consumer. In particular, the pad members 104 and 106 create a target zone for attaching the signaling device and the conductive leads or elements.

Referring to FIG. 3, for exemplary purposes, a signaling device 110 is shown attached to the conductive pad members 104 and 106. As shown, in this aspect, the signaling device generally 110 includes a transmitter 112 and a receiver 114. The transmitter 112 includes a pair of opposing terminals that are electrically connected to the corresponding conductive pad members. When a body fluid is present in the absorbent article 20, the open circuit formed by the conductive elements 100 and 102 is closed which, in turn, activates the signaling device 110. In particular, in this aspect, the transmitter 112 sends a wireless signal to the receiver 114 which then indicates to a user that a body fluid is present in the absorbent article.

The signaling device 110 can emit an audible signal or a visual signal to indicate to the user that the circuit has been closed. The audible signal, for instance, may be as simple as one or more beeps to perhaps emitting a musical tune. Similarly, if the signaling device 110 issues a visible signal, the visible signal may comprise a few lights or an interactive display. In still another aspect, the receiver 114 of the signaling device 110 may be configured to vibrate when the circuit within the absorbent article is closed.

As described above, the signaling device 110 can be configured to indicate the presence of any suitable conductive fluid within the absorbent article 20. The fluid may include, for instance, urine, a metabolite, and the like.

In the aspect shown in FIG. 3, the signaling device 110 includes a transmitter 112 in combination with a receiver 114. It should also be understood, however, that the signaling device may comprise a single unit that remains attached to the absorbent article 20. For example, the signaling device may be mounted on the absorbent article and issue a visible signal and/or an audible signal from the article itself.

Absorbent articles, such as the absorbent article 20 as shown in FIG. 1, are typically made in process lines at very fast rates. Detecting foreign material in the absorbent articles already including metallic components at such fast speeds can be problematic. In this regard, the present disclosure, in one aspect, is directed to a process for quickly checking the quality of the produced products. In particular, the process can be used to assist in verifying that the absorbent articles made with a wetness sensing system do not include foreign material.

Figure 4:
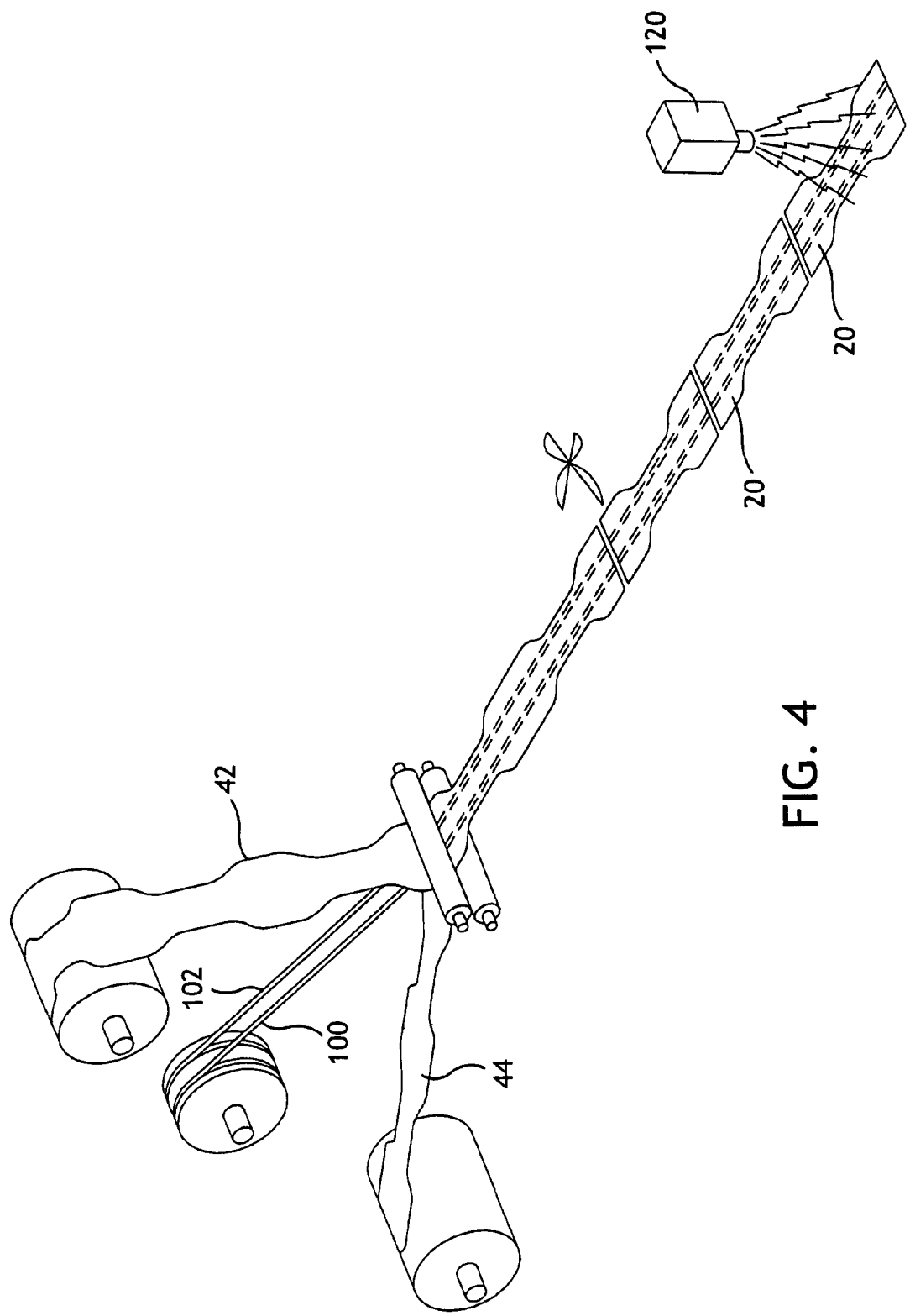
FIG. 4 is one aspect of a process for producing absorbent articles in accordance with the present disclosure.

For instance, referring to FIG. 4, a simplified process diagram is shown for producing the absorbent articles 20. In this regard, it should be understood that a commercial absorbent article production line is relatively complicated with a significant number of moving equipment that constantly provides certain parts to the article as it is produced. Thus, the illustration provided by FIG. 4 is for exemplary purposes only.

As shown in FIG. 4, a bodyside liner 42 in combination with an absorbent structure are fed into a process line with an outer cover 44. In addition, conductive elements 100 and 102 are also fed into the process to form at least a portion of a wetness sensing system. In this aspect, the conductive elements 100 and 102 are positioned in between the outer cover 44 and the bodyside liner 42. Once the materials are laminated together, a cutting step takes place to form the absorbent articles 20.

In accordance with the present disclosure, verification that the absorbent articles including a wetness sensing system do not include foreign material includes passing the absorbent articles in close proximity to a foreign material sensor 120. The foreign material sensor 120 is configured to detect the presence of any foreign material within the absorbent articles 20.

In general, any suitable foreign material sensor consistent with this disclosure may be incorporated into the process of the present disclosure. The particular foreign material sensor selected, for instance, may depend upon the type of material used to construct the conductive elements 100 and 102 and the amount of sensitivity that is desired for the application.

In one aspect of the present disclosure, a foreign material sensor 120 in the form of a commercially-available x-ray machine is incorporated into the process to inspect individual absorbent articles 20 or packages of absorbent articles 20. Such an x-ray machine can be capable of detecting not only metallic foreign material, but also mineral clumps of materials such as super absorbents and glass contaminants.

In one exemplary aspect of the present disclosure, the foreign material sensor 120 may be an GORING KERR EZx model x-ray system available from Thermo Electron Corporation in Boston, Mass. Such an x-ray system is sensitive for ferrous, non-ferrous, and stainless steel contaminants and is as good, or in many applications better, than that of competing metal detectors. Multiple aperture sizes and line heights provides such an x-ray system with configuration flexibility to suit a wide range of products and production lines.

X-ray systems generally work by interposing an article to be inspected between an x-ray source and an x-ray detector. The x-rays emitted by the source are absorbed to varying degrees by substances within the article being inspected, with the x-ray detector detecting the x-rays that pass through the article. The x-ray detector then communicates with its associated hardware and/or software to present an image of the article in a form usable to a user or another system within the process.

The foreign material sensor 120, as shown in FIG. 4, can be configured to provide various information about the absorbent articles 20 depending upon the particular application. For example, in one aspect, the foreign material sensor 120 may be used simply to confirm that a foreign material is not present within the absorbent article. In this aspect, for instance, the foreign material sensor 120 may produce a signal, such as an audible or visual signal, when the absorbent article includes a foreign material or, alternatively, when an absorbent article does not include a foreign material.

In other aspects, however, more sophisticated sensors may be used. For instance, in an alternative aspect, the foreign material sensor 120 may be configured to detect whether or not a foreign material is present in the absorbent article 20 within a pre-selected range or above a pre-selected setpoint. Thus, should the absorbent article include too little foreign material and/or include too much foreign material, a signal may be generated indicating a possible manufacturing flaw.

The foreign material sensor 120 can also be configured and/or programmed to not only sense a pre-selected amount of foreign material, but can also be configured to only sense certain types of materials. For example, foreign material sensors 120 are capable of discerning between various different materials. For instance, in one aspect, the foreign material sensor 120 may be capable of discerning between ferrous materials and non-ferrous materials. In other aspects, the foreign material sensor 120 may also be configured to discriminate between different types of metals, such as iron, steel, gold, nickel, copper, zinc, brass and silver. Depending upon the type of material used to produce the conductive elements 100 and 102, the foreign material sensor 120 may be configured so as to only detect materials other than that particular type of material.

Having a foreign material sensor 120 with selectivity as described above is typically referred to as the process of using "discrimination." Thus, the foreign material sensor 120 can be configured to only detect certain types of foreign materials and can also be configured so as to detect those particular types of foreign materials within particular ranges. In one particular aspect, for instance, ferrous materials may be used to produce the conductive elements 100 and 102. In this aspect, if desired, the foreign material sensor 120 can be configured to only sense non-ferrous materials.

In the aspect illustrated in FIG. 4, the absorbent articles 20 are passed below the foreign material sensor 120 during production of the articles. According to the present disclosure, however, the articles can be checked at other times during the production and packaging of the articles. For example, in one aspect, it may be desirable to conduct a quality control test on the articles after the articles have been packaged. For example, referring to FIG. 5, a package 122 of absorbent articles 20 is illustrated. In this aspect, each of the absorbent articles 20 includes a wetness sensing system. The wetness sensing system, for instance, may include a pair of metallic conductive elements 100 and 102. The absorbent articles 20, in this aspect, are enclosed within a shrink-wrapped package. It should be understood, however, that the process of the present disclosure can be carried out on any suitable type of package.

In accordance with the present disclosure, the package 122 is placed in proximity to a foreign material sensor 120. In this aspect, the foreign material sensor 120 is configured to be portable and scanned over the package. Alternatively, such as shown in FIG. 4, the foreign material sensor 120 may be positioned at a fixed location and the package 122 may be conveyed, such as on a conveyor, in close proximity to the detector.

Figure 5:
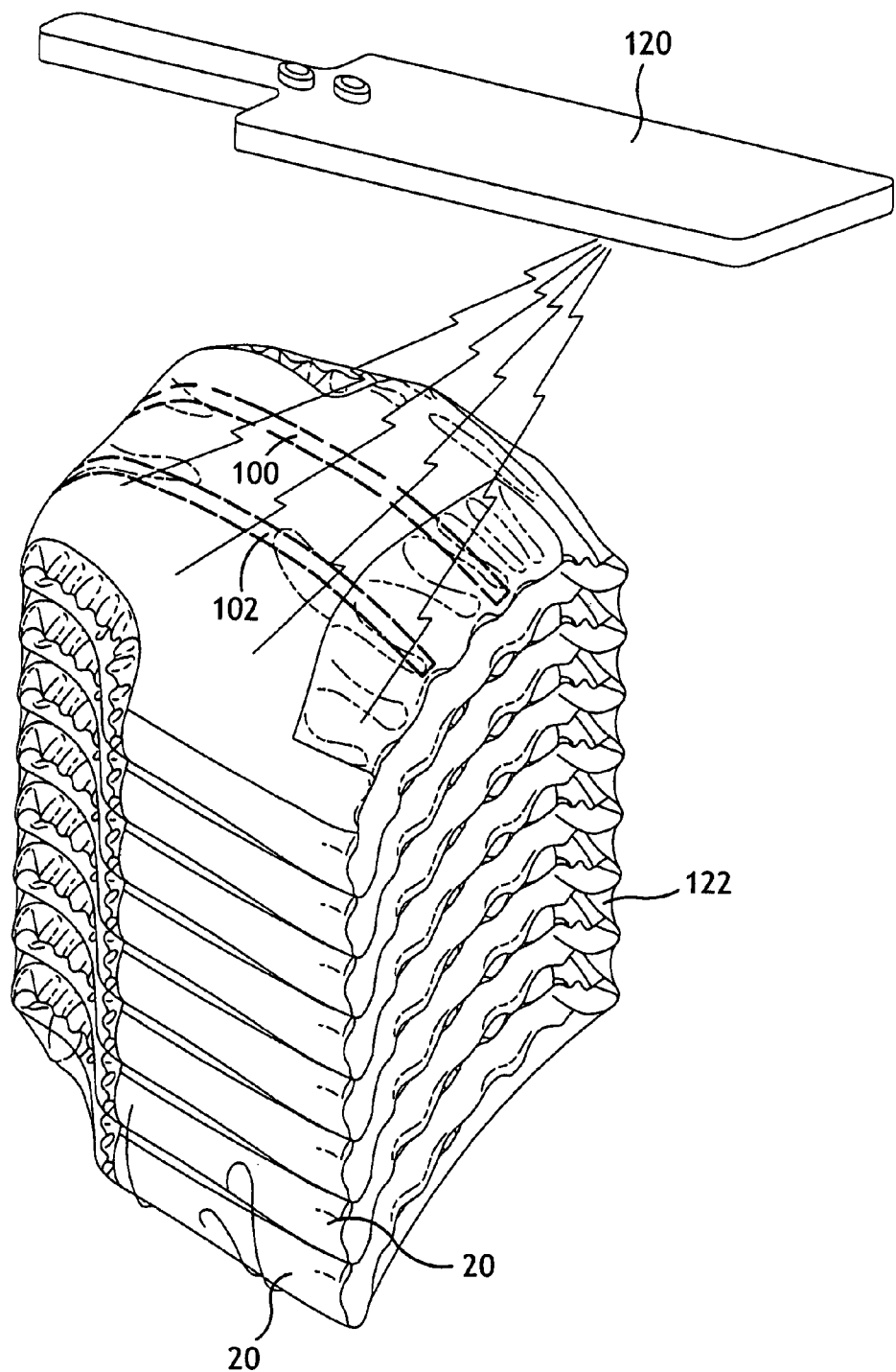
FIG. 5 is a perspective view of another aspect of a process in accordance with the present disclosure for determining the presence of foreign material within a package of absorbent articles.

As shown in FIG. 5, the foreign material sensor 120 is passed in proximity to the package 122 to confirm the presence of wetness sensing systems within the individual absorbent articles and/or the absence of foreign material in the articles 20 or package 122. In particular, the package 122 may be placed in proximity to the foreign material sensor 120 so that the foreign material sensor 120 can detect whether the package includes a sufficient amount of foreign material to require the package 122 to be culled. In one particular aspect, for example, the foreign material sensor 120 can be configured to generate a signal when the package 122 includes the foreign material in an amount outside of a pre-selected range or above a pre-selected setpoint. For instance, the foreign material sensor 120 may release an audible signal or a visual signal when the package includes more foreign material than it should and/or less foreign material than it should. In an alternative aspect, instead of releasing an audible or visual signal, the foreign material sensor 120 may release some other type of electric signal that then removes the package 122 from a conveyor line and places it in a bin designed to hold defective product.

In the process illustrated in FIG. 5, in one aspect, the package 122 can be scanned by the foreign material sensor 120 at the location at which the package is formed.

These and other modifications and variations to the present disclosure may be practiced by those of ordinary skill in the art, without departing from the spirit and scope of the present disclosure, which is more particularly set forth in the appended claims. In addition, it should be understood that aspects of the various aspects may be interchanged both in whole or in part. Furthermore, those of ordinary skill in the art will appreciate that the foregoing description is by way of example only, and is not intended to limit the disclosure so further described in such appended claims.

What is claimed:

1. A process for controlling the quality of manufactured absorbent articles, the process comprising:

incorporating into an absorbent article at least a portion of a wetness sensing system that is configured to detect the presence of a substance, the portion of the wetness sensing system incorporated into the absorbent article comprising at least one metallic conductive element; and passing the absorbent article in proximity to a foreign material sensor employing x-ray technology, the foreign material sensor adapted to detect the presence of foreign material to confirm whether metallic foreign material has been incorporated into the article.

2. A process as defined in claim 1, further comprising packaging together a plurality of absorbent articles each incorporating at least a portion of a wetness sensing system and passing the package in proximity to the foreign material sensor, the foreign material sensor being configured to indicate whether the package include foreign material.

3. A process as defined in claim 2, wherein the package is passed in proximity to the foreign material sensor prior to being shipped from a location where the absorbent articles are packaged together.

4. A process as defined in claim 1, wherein the foreign material sensor operates by generating x-rays.

5. A process as defined in claim 1, wherein the foreign material sensor is configured to indicate whether each absorbent article includes foreign material above a selected setpoint.

6. A process as defined in claim 5, wherein the foreign material sensor produces a signal when the amount of foreign material included within the absorbent article is above the selected setpoint.

7. A process as defined in claim 6, wherein the signal is audible or visual.

8. A process as defined in claim 1, wherein the foreign material sensor is adapted to communicate with process control and/or monitoring equipment through wired or wireless means.

9. A process as defined in claim 1, wherein the foreign material detected by the foreign material sensor comprises a ferrous material and wherein the foreign material sensor is configured to detect only ferrous metals.

10. A process as defined in claim 1, wherein the foreign material detected by the foreign material sensor comprises a non-ferrous material and wherein the foreign material sensor is configured to detect only non-ferrous metals.

11. A process as defined in claim 1, wherein the wetness sensing system includes a first material and wherein the foreign material sensor is configured to detect the presence of the first material, the foreign material sensor also being configured to independently detect the presence of a foreign material for confirming that the package does not include such foreign material.

* * * * *